United States Patent
Nakano et al.

(10) Patent No.: US 7,799,537 B2
(45) Date of Patent: Sep. 21, 2010

(54) CHOLESTEROL MEASURING REAGENT CONTAINING A CHOLESTEROL ESTERASE

(75) Inventors: Takamitsu Nakano, Maebashi (JP); Manabu Nimi, Takasaki (JP); Fumiko Ogihara, Fujioka (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 191 days.

(21) Appl. No.: 11/720,338

(22) PCT Filed: Nov. 28, 2005

(86) PCT No.: PCT/JP2005/021757

§ 371 (c)(1), (2), (4) Date: May 29, 2007

(87) PCT Pub. No.: WO2006/057377

PCT Pub. Date: Jun. 1, 2006

(65) Prior Publication Data

US 2008/0268461 A1    Oct. 30, 2008

(30) Foreign Application Priority Data

Nov. 29, 2004    (JP)    ............... 2004-344427

(51) Int. Cl.
*C12Q 1/60*    (2006.01)
(52) U.S. Cl. .......................... 435/11; 435/19
(58) Field of Classification Search ............ 435/11, 435/19
See application file for complete search history.

(56) References Cited

U.S. PATENT DOCUMENTS 6,986,998 B2 *  1/2006  Kishi et al. ................ 435/11

2003/0207342 A1 * 11/2003 Miyauchi .................... 435/11
2009/0023167 A1 *  1/2009 Miyauchi et al. ............ 435/11

FOREIGN PATENT DOCUMENTS

| EP | 1 132 482 B1 | 5/2003 |
| JP | 03-245058 | 10/1991 |
| JP | 2001-231597 | 8/2001 |
| JP | 3251304 | 11/2001 |

OTHER PUBLICATIONS

Domyakukoka (Arteriosclerosis), vol. 25, No. 9-10, 1998, Partial English Translation, pp. 371-376.
Kugiyama, Kiyotaka et al., "Remnant Lipoprotein Levels in Fasting Serum Predict Coronary Events in Patients With Coronary Artery Disease", Circulation, vol. 99, pp. 2858-2860, 1999.
Wang, Tao et al., "Ratio of Remnant-like Particle-Cholesterol to Serum Total Triglycerides Is an Effective Alternative to Ultracentrifugal and Electrophoretic Methods in the Diagnosis of Familial Type III Hyperlipoproteinemia", Clinical Chemistry, vol. 45, No. 11, pp. 1981-1987, 1999.
Nakano, Takamitsu et al., "Remnant-like lipoprotein Cholesterols", Clinical assay, vol. 44, No. 10, pp. 1114-1120, 2000.
U.S. Appl. No. 12/158,326, filed Jun. 20, 2008, Ogihara, et al.

* cited by examiner

*Primary Examiner*—Ralph Gitomer
(74) *Attorney, Agent, or Firm*—Oblon, Spivak, McClelland, Maier & Neustadt, L.L.P.

(57) ABSTRACT

There are provided a method and reagent for measuring cholesterol in remnant-like lipoprotein in a sample with high sensitivity by more simple operation. The method for measuring cholesterol in remnant-like lipoprotein uses a cholesterol esterase, in which the activity ratio of a lipoprotein lipase to a cholesterol esterase (lipoprotein lipase activity/cholesterol esterase activity) is from 12 to 7000 in a method for measuring cholesterol in the lipoprotein by measuring hydrogen peroxide or a reduced coenzyme obtained by allowing the cholesterol esterase and a cholesterol oxidase or a cholesterol dehydrogenase to act on a test sample containing a lipoprotein.

8 Claims, 5 Drawing Sheets

Fig. 4   Addition of Antibodies (JI-H:100 μg/ml, H-12:100 μg/ml)
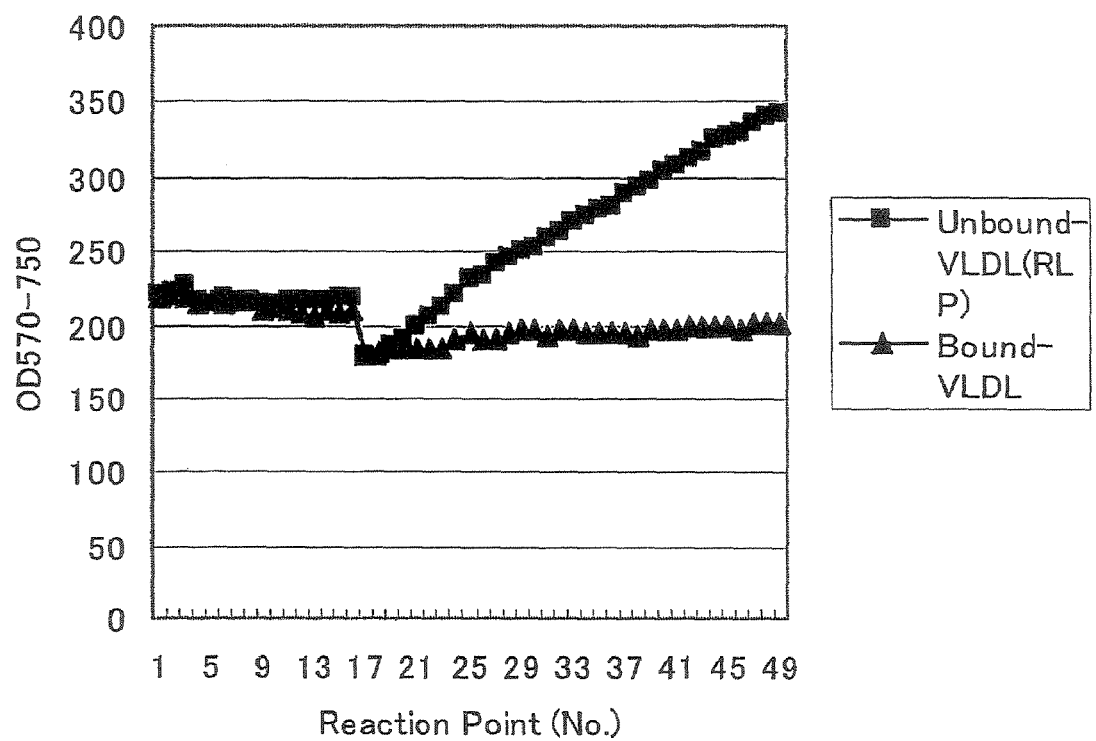

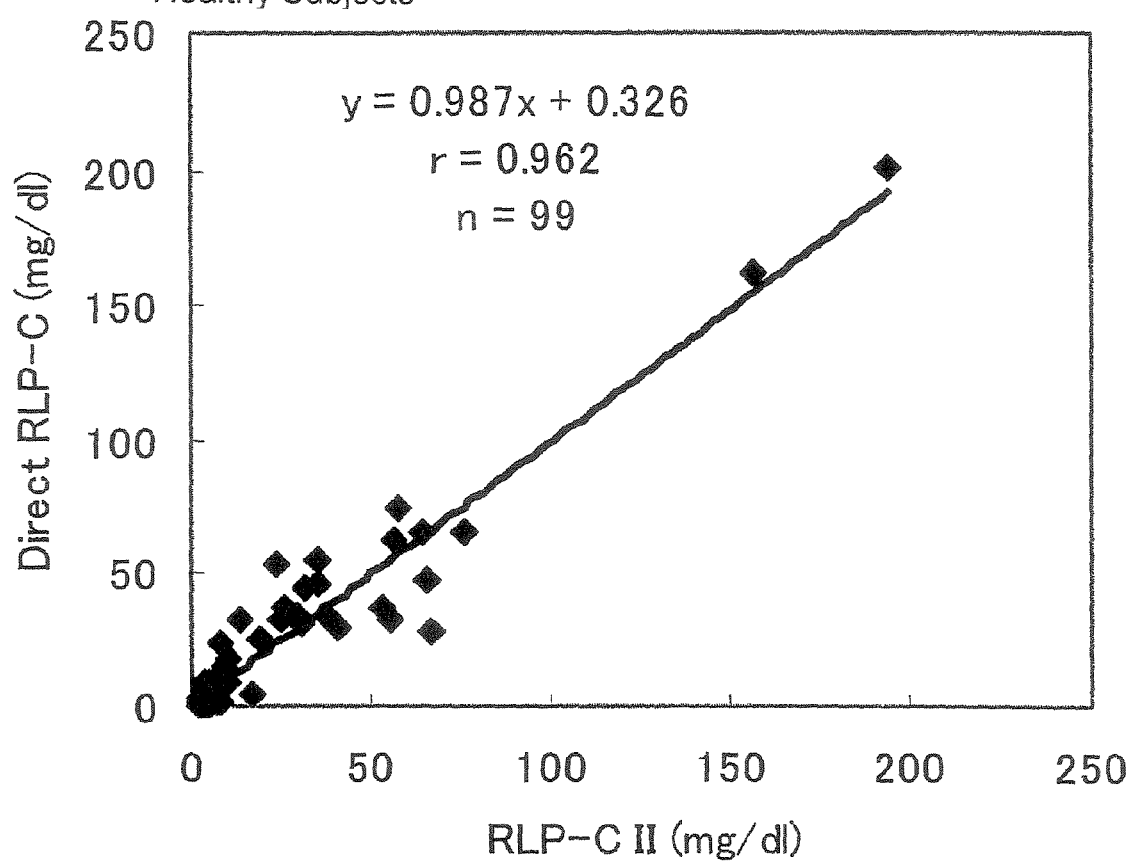
Fig. 5 Corelation between RLP-C II and Direct RLP-C in Coronary Artery Disease Patients, Hyperlipidemia Patients and Healthy Subjects

CHOLESTEROL MEASURING REAGENT CONTAINING A CHOLESTEROL ESTERASE

TECHNICAL FIELD

The present invention relates to a method for measuring cholesterol in remnant-like lipoprotein, and also to a measuring reagent for cholesterol in remnant-like lipoprotein.

BACKGROUND ART

With the recent trend toward aging society, the morbidity of adult diseases is rapidly increasing. In particular, arteriosclerosis is well known as one of the primary factors causative of circulatory system diseases, such as heart diseases and cerebrovascular diseases (including brain infarction).

The accumulation of cholesterol on blood vessels plays an essential role in the growth of arteriosclerosis, and is associated with various lipoproteins in blood. Lipoproteins include cholesterol, cholesterol ester, neutral fat, phospholipid, and apoprotein as components. Of these lipoproteins, cholesterol in high density lipoprotein (HDL) is known as a negative risk factor for arteriosclerosis, whereas cholesterol in low density lipoprotein (LDL) is known as a positive risk factor for arteriosclerosis. These cholesterols are frequently observed in the field of clinical diagnosis.

In recent years, however, it has been reported that the cholesterol in a lipid metabolism-induced lipoprotein such as remnant-like lipoprotein, rather than the LDL cholesterol, is a more closely related indicator as the risk factor for arteriosclerosis. From the viewpoint of such problems, it is increasingly becoming necessary to develop a technological method for measuring cholesterols in lipoprotein in biological samples more easily and efficiently.

Among the conventionally existing methods for enzymatically measuring cholesterol in remnant-like lipoprotein, there are reports disclosing a method characterized by increasing a measurement selectivity by using a gel on which an antibody to an apoprotein as a component of lipoprotein is immobilized or by using a phospholipid-degrading enzyme, a surfactant, or the like, allowing cholesterol esterase and cholesterol oxidase or cholesterol dehydrogenase to act so that cholesterol ester is converted into cholesterol, and then measuring the produced hydrogen peroxide or reduced coenzyme (see Patent Documents 1 and 2 and Non-Patent Document 1).

Even such methods, however, have advantages and disadvantages in terms of selectivity to remnant-like lipoprotein, easiness of operation, measurement time period, and the like, and thus are not necessarily sufficient.

Patent Document 1: Japanese Patent Application Laid-Open (JP-A) No. 2001-231597.

Patent Document 2: Japanese Patent No. 2949354

Non-Patent Document 1: Domyakukoka (arteriosclerosis) 25 (9, 10), 371 (1998)

DISCLOSURE OF THE INVENTION

Problem to be Solved by the Invention

It is an object of the present invention to provide a method for more easily and precisely measuring cholesterol in remnant-like protein and to provide a reagent for use in performing such a method.

Means for Solving the Problems

In light of the circumstances, the inventors have focused on the fact that many cholesterol esterases have not only esterase activity but also not a little lipoprotein lipase activity and investigated various conditions for the measurement of cholesterol in lipoprotein. As a result, it has been found that if a cholesterol esterase in which the rate of the activity of lipoprotein lipase is higher than that of cholesterol esterase is selected and used with cholesterol oxidase or cholesterol dehydrogenase to measure cholesterol in lipoprotein, the selectivity to remnant-like lipoprotein will be high, and cholesterol in remnant-like lipoprotein can be selectively measured from biological samples containing lipoproteins such as high density lipoprotein (HDL), low density lipoprotein (LDL) chylomicron (CM), very low density lipoprotein (VLDL), CM remnant, VLDL remnant, and intermediate density lipoprotein (IDL) remnant.

Thus, the present invention is directed to a method for measuring cholesterol in remnant-like lipoprotein, characterized in that a cholesterol esterase, in which the activity ratio of a lipoprotein lipase to a cholesterol esterase (lipoprotein lipase activity/cholesterol esterase activity) is from 12 to 7000, is used, in a method for measuring cholesterol in the lipoprotein by measuring hydrogen peroxide or a reduced coenzyme obtained by allowing the cholesterol esterase and a cholesterol oxidase or a cholesterol dehydrogenase to act on a test sample containing a lipoprotein.

The present invention is also directed to a measuring reagent for cholesterol in remnant-like lipoprotein, including: a cholesterol esterase in which the activity ratio of a lipoprotein lipase to a cholesterol esterase (lipoprotein lipase activity/cholesterol esterase activity) is from 12 to 7000; and a cholesterol oxidase or a cholesterol dehydrogenase.

EFFECTS OF THE INVENTION

When the measurement method and the measurement reagent according to the present invention are used, cholesterol in remnant-like lipoprotein can be very easily measured with high sensitivity in a short time.

BRIEF DESCRIPTION OF DRAWINGS

FIG. 4 is a graph showing the reactivity with respect to unbound-VLDL and bound-VLDL in a case where antibodies are added; and FIG. 5 is a graph showing a correlation between the measurement method of the present invention and an existing measurement method (RLP-II) when remnant-like lipoprotein in blood is measured.

BEST MODE FOR CARRYING OUT THE INVENTION

Figure 1:
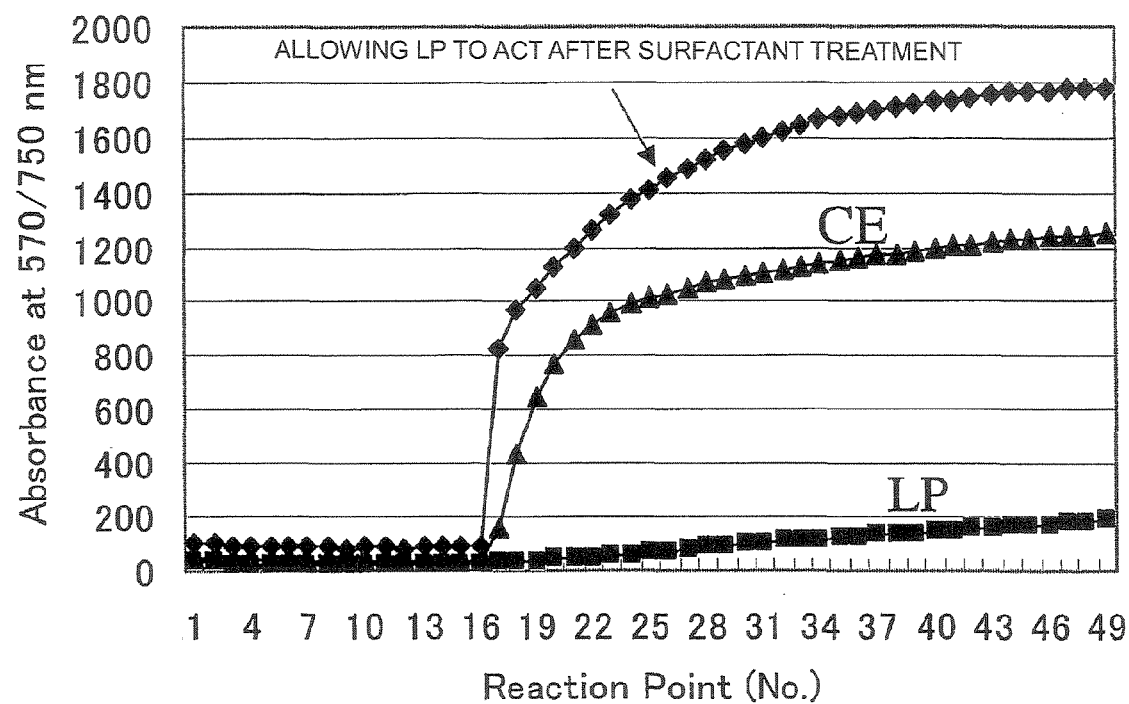
FIG. 1 is a graph showing the reaction specificity with respect to LDL in a case where an LP enzyme is used.

According to the present invention, the method for measuring cholesterol in remnant-like lipoprotein is performed as follows: hydrogen peroxide or a reduced coenzyme obtained by allowing the cholesterol esterase and a cholesterol oxidase or a cholesterol dehydrogenase to act is measured and a cholesterol esterase, in which the activity ratio of lipoprotein lipase (LPL) to cholesterol esterase (CE) (lipoprotein lipase activity/cholesterol esterase activity) is from 12 to 7000, is used.

Cholesterol esterase is an enzyme that can hydrolyze cholesterol esters in lipoproteins to produce cholesterol. It is known that in many cases, this enzyme has not only the esterase activity but also not a little lipoprotein lipase activity, that is, lipase activity hydrolyzing neutral fat. In the present invention, it is necessary to use a cholesterol esterase having a lipoprotein lipase activity stronger than the cholesterol esterase activity, and specifically it is necessary to use a cholesterol esterase in which the activity ratio of lipoprotein lipase to cholesterol esterase (lipoprotein lipase activity/cholesterol esterase activity) is from 12 to 7000, so that the enzyme can selectively act on remnant-like lipoprotein to allow selective hydrolysis of cholesterol ester in the protein. Therefore only the desired cholesterol in the remnant-like lipoprotein can be selectively measured.

Herein, the lipoprotein lipase activity refers to an activity unit that is calculated according to a lipoprotein lipase activity analysis method using an olive oil emulsion (Horiuchi Y. et al., J Biochem 1976; 80:367-370), and the cholesterol esterase activity refers to an activity unit that is calculated according to a CEN activity analysis method using a calf serum (Kameno Y. et al., Jap J Clin Path 1976; 24:650).

The activity ratio of the lipoprotein lipase to the cholesterol esterase (lipoprotein lipase activity/cholesterol esterase activity) (hereinafter also simply referred to as "activity ratio") is from 12 to 7000, preferably from 20 to 1000, more preferably from 28 to 800.

Examples of the cholesterol esterase having such an activity ratio include LP (with an activity ratio of 460 to 800, manufactured by Asahi Kasei Pharma Corporation), LPBP (with an activity ratio of 5600 to 6900, manufactured by Asahi Kasei Pharma Corporation), CEN (with an activity ratio of 13.0 to 16.0, manufactured by Asahi Kasei Pharma Corporation), CE (with an activity ratio of 13.0 to 16.0, manufactured by Amano Enzyme Inc.), COE 311 (with an activity ratio of 28.0 to 35.0, manufactured by Toyobo Co., Ltd.), and enzymes having the same activity ratio as any of the above.

The cholesterol esterase may be any of a microorganism-derived enzyme and an animal-derived enzyme, as long as it satisfies the above conditions.

The amount of the cholesterol esterase may be usually in the range of 0.1 to 200 units/mL, preferably of 1 to 100 units/mL, depending on the content or physical properties of the remnant-like lipoprotein in the test sample. Generally for healthy subjects, good measurement results can be obtained with an amount of 1 to 5 units/mL.

Here, at least 50 units/mL of the cholesterol esterase should preferably be used for hyperlipemia patients, particularly for patients with type III familial hyperlipemia, for which a simple measurement method has ever been demanded. For healthy pregnant women, in which an increase in cholesterol value in blood is generally observed, good measured values can be obtained using 20 units/mL of the cholesterol esterase according to the present invention.

According to the present invention, the method for measuring cholesterol in remnant-like lipoprotein may include pretreating the test sample with an anti-apoB-100 antibody and/or an anti-apoA-I antibody. The addition of the antibody can increase the selectivity of the cholesterol esterase to LDL or VLDL having as a component and HDL or CM having an apoA-I as a component.

Such an antibody treatment technique is disclosed in Japanese Patent No. 2949354, in which the operation procedure includes adding an antibody-bound gel to a test sample and allowing it to stand for several hours to separate remnant-like lipoprotein from other lipoproteins (HDL, LDL, VLDL, CM) so that the selectivity of cholesterol esterase is secondarily increased. In contrast, when the cholesterol esterase according to the present invention is used, there is no need to immobilize the antibody on a gel, and the action of the enzyme on other lipoproteins than remnant-like lipoprotein can be inhibited only by adding the antibody. As a result, the selectivity to the remnant-like lipoprotein can be increased. In the former method, the gel-immobilized antibody must be allowed to stand for a long time after the addition. According to the method of the present invention, however, the object is achieved by the binding between the antibody and lipoprotein, and therefore, the next operation may be performed several minutes after the addition, so that dramatic improvements can be made in the simplicity, measurement accuracy and time reduction of the procedure.

Any antibody to apoB-100 or apoA-I may be used without particular limitations, and the antibody to be used may be any of a polyclonal antibody, a monoclonal antibody and a combination thereof. An example of the apoB-100-recognizing antibody includes JI-H (manufactured by JIMRO Co., Ltd.), and an example of the apoA-I-recognizing antibody includes H-12 (manufactured by JIMRO Co., Ltd.). The amount of addition of the antibody depends on the amount of HDL, LDL, VLDL, or CM in the test sample. Therefore the addition of the antibody in such an amount that it can bind to the lipoprotein should be sufficient.

The cholesterol oxidase may be any enzyme having the ability to oxidize cholesterol and produce hydrogen peroxide, examples of which include microorganism- or animal-derived cholesterol oxidases.

The cholesterol dehydrogenase may be any enzyme having the ability to oxidize cholesterol and reduce oxidized coenzyme examples of which include microorganism- or animal-derived cholesterol dehydrogenases.

The cholesterol oxidase and the cholesterol dehydrogenase are each preferably used in an amount of 0.01 to 200 U/mL, more preferably of 0.1 to 100 U/mL, in a reaction liquid.

Besides the cholesterol esterase, cholesterol oxidase and cholesterol dehydrogenase, various types of metal ions, particularly Ca ions may be added to increase the specificity and stability of the enzyme in the measurement method of the present invention.

The cholesterol esterase, cholesterol oxidase or cholesterol dehydrogenase may be chemically modified with a group including polyethylene glycol as a main component, a water-soluble oligosaccharide residue, a sulfopropyl group, or the like, as long as modification has the same activity, or the cholesterol esterase, cholesterol oxidase or cholesterol dehydrogenase may be a modified enzyme having the same activity obtained by genetic engineering thereto.

The enzyme reaction according to the present invention may be performed in an aqueous medium, and in particular it is preferably performed in a buffer.

Examples of the buffer include tris(hydroxymethyl)aminomethane, phosphate buffers, borate buffers, and Good's buffers. Examples of Good's buffers include N-(2-acetamido)-2-aminoethanesulfonic acid (ACES), N-(2-acetamido)iminodiacetic acid (ADA), N,N-bis(2-hydroxyethyl)-2-aminoethanesulfonic acid (BES), 3-[N,N-bis(2-hydroxylethyl)amino]-2-hydroxypropanesulfonic acid (DIPSO), 2-(2-hydroxyethyl)piperazine-NI-2-ethanesulfonic acid (HEPES), 3-(N-morpholino)propanesulfonic acid (MOPSO), piperazine-N,N'-bis(2-ethanesulfonic acid) (PIPES), and piperazine-N,N'-bis(2-hydroxypropane-3-sulfonic acid) (POPS).

The buffer may have a pH of 4 to 10, preferably of 5 to 9. The buffer is preferably used at a concentration of 5 to 500 mM, more preferably of 10 to 200 mM, particularly preferably of 20 to 100 mM.

When the cholesterol esterase and the cholesterol oxidase are used in the measurement method of the present invention, hydrogen peroxide is produced from oxygen by the reaction of cholesterol. For example, the produced hydrogen peroxide may be quantified using 4-aminoantipyrine and phenols, 4-aminoantipyrine and Trinder's reagents, or a highly-sensitive chromogen, in the presence of peroxidase.

Examples of the phenols include phenol, 4-chlorophenol, m-cresol, and 3-hydroxy-2,4,6-triiodobenzoic acid (HTIB).

Examples of the Trinder's reagents (see the union catalog, 19th Edition, 2002, published by DOJINDO LABORATORIES) include anilines such as N-sulfopropylaniline, N-ethyl-N-(2-hydroxy-3-sulfopropyl)-m-toluidine (TOOS), N-ethyl-N-(2-hydroxy-3-sulfopropyl)-3,5-dimethylaniline (MAOS), N-ethyl-N-(2-hydroxy-3-sulfopropyl)-3,5-dimethoxyaniline (DAOS), N-ethyl-N-sulfopropyl-m-toluidine (TOPS), N-(2-hydroxy-m-toluidine, N,N-disulfopropyl-3,5-dimethoxyaniline, N-ethyl-N-sulfopropyl-m-anisidine, N-ethyl-N-sulfopropylaniline, N-ethyl-N-sulfopropyl-3,5-dimethoxyaniline, N-sulfopropyl-disulfopropyl-3,5-dimethoxyaniline, N-ethyl-N-sulfopropyl-3,5-dimethylaniline, N-ethyl-N-(2-hydroxy-3-sulfopropyl)-m-anisidine, N-ethyl-N-(2-hydroxy-3-sulfopropyl)aniline, N-ethyl-N-(2-hydroxy-3-sulfopropyl)-3,5-dimethoxyaniline, N-ethyl-m-3-sulfopropyl-3-methoxyaniline (APPS), N-ethyl-N-3-sulfopropylaniline (ALPS), and N-ethyl-N-2-hydroxy-3-sulfoproxyl-3-methoxyaniline; or N-ethyl-N-(3-methylphenyl)-N'-succinylethylenediamine (EMSE), or N-ethyl-N-(3-methylphenyl)-N'-acetylethylenediamine.

Examples of the highly-sensitive chromogens include 10-(N-methylcarbamoyl)-3,7-bis(dimethylamino)phenothiadine (MCDP) disclosed in Japanese Patent Application Publication (JP-B) No. 60-33479, bis[3-bis(4-chlorophenyl)methyl-4-dimethylaminopheny]amino (BCMA) disclosed in JP-B No. 4-27839, and the compounds disclosed in JP-A No. 62-296. The concentration of the chromogens is preferably from 0.01 to 10 mg/mL.

When the cholesterol esterase and the cholesterol dehydrogenase are used, NAD(P)H which is a reduced coenzyme, is produced from NAD(P) which is an oxidized coenzyme, by the reaction of cholesterol. NAD(P)H may be quantified by measuring the absorbance of the reaction liquid at a wavelength of about 300 to about 500 nm, preferably of 330 to 400 nm, particularly preferably at about 340 nm. NAD(P)H may also be quantified by a process including adding diaphorase and a tetrazolium salt to form a formazan dye and determining the formazan dye by colorimetry.

The reaction may be performed at 10 to 50° C., preferably at 30 to 40° C., generally at 37° C. for 1 to 30 minutes, preferably for 2 to 10 minutes.

The reagent according to the present invention includes a cholesterol esterase in which lipoprotein lipase activity is stronger than the cholesterol esterase activity and includes cholesterol oxidase or cholesterol dehydrogenase.

For example, in a case where other lipoproteins than remnant-like lipoprotein are significantly present in the test sample, pretreatment with the anti-apoB-100 antibody and the anti-apoA-I antibody may be performed in order to reduce the effect of the lipoproteins. In such a case, the reagent preferably includes a first reagent containing the antibody and a second reagent containing the enzyme solution. In this case, it is preferred that the first reagent should be added to the test sample and allowed to react at 25 to 40° C. for 1 to 10 minutes, and then the second reagent should be added and allowed to act at 25 to 40° C. for 2 to 20 minutes.

If necessary, the measuring reagent may contain various salts for solubilizing proteins such as globulins in the biological sample, lipoprotein coagulants, and other enzymes.

Examples of the salts include sodium chloride, sodium sulfate, potassium chloride, potassium sulfate, magnesium chloride, magnesium sulfate, magnesium acetate, lithium chloride, lithium sulfate, ammonium sulfate, magnesium nitrate, and calcium nitrate, and the salts may be used at 0 to 100 mM. Examples of the lipoprotein coagulant include polyanions such as phosphotungstate, dextran sulfate and heparin, and salts of divalent metals such as magnesium, calcium and cobalt. Examples of other enzymes include ascorbate oxidase.

In the present invention, any test sample may be used without particular limitations. Specifically, biological samples such as blood itself (whole blood) or blood plasma, and blood fractions such as blood serum may be used.

EXAMPLES

The present invention is described in more detail by showing the examples below, which are not intended to limit the scope of the present invention.

Example 1

(1) Preparation of Sample

Serum component was separated into an LDL fraction and an HDL fraction, and each lipoprotein was measured. The method of protein fractionation is described below. An anti-apoB-100 antibody-bound affinity column and an anti-apoA-I antibody-bound affinity column were prepared, respectively. Blood serum was added thereto, and bound fractions were collected and assigned as LDL and HDL, respectively. VLDL fractions were separated by ultracentrifugation (Havel R. J. et al., J Clin Invest, 1955; 34:1345, 120,000 rpm, 1.5 hr. 4° C.) (Total VLDL) and then a fraction bound by immunoabsorption (with an anti-apoB-100 antibody-bound affinity column) was assigned as Bound-VLDL, while the pass-through fraction was assigned as Unbound-VLDL (remnant-like lipoprotein fraction). In both of measurements in Examples 2 and 3, samples with an adjusted cholesterol concentration of 40 mg/dL were used in the measurement.

(2) Preparation of Measuring Reagents

Reagents for measuring cholesterol in remnant-like lipoprotein were prepared as shown below.

TABLE 1

| Reagent 1 (for Pretreatment with Antibodies) | |
| --- | --- |
| Good's buffer pH 6.8 (PIPES, manufactured by DOJINDO LABORATORIES) | 50 mM |
| HDAOS (manufactured by DOJINDO LABORATORIES) | 1 mM |
| Anti-apoB-100 monoclonal antibody (JI-H, manufactured by JIMRO Co., Ltd.) | 100 µg/mL |
| Anti-apoA-I monoclonal antibody (H-12, manufactured by JIMRO Co., Ltd.) | 100 µg/mL |

TABLE 2

| Reagent 2 | |
|---|---|
| Good's buffer pH 6.8 (BES, manufactured by DOJINDO LABORATORIES) | 50 mM |
| Cholesterol esterase LP (manufactured by Asahi Kasei Pharma Corporation) or CE (manufactured by Amano Enzyme Inc.) | 20 units/mL |
| 4-aminoantipyrine (manufactured by KANTO CHEMICAL CO., INC) | 3 mM |
| Peroxidase (manufactured by Amano Enzyme Inc.) | 10 units/mL |
| Cholesterol oxidase (manufactured by Amano Enzyme Inc.) | 6 units/mL |

(3) Measurement Method and Results

When the antibody pretreatment was performed, 210 μL of Reagent 1 was added to the cell of a spectrophotometer, and 20 μL of blood serum was added thereto and stirred and then incubated at 37° C. Subsequently, after five minutes (Reaction Point 17), 70 μL of Reagent 2 preincubated at 37° C. was added thereto, and then the measurement was performed until five minutes later (Reaction Point 33). The measurement was performed at a main wavelength of 572 nm and a subwavelength of 748 nm.

Evaluation was made based on the change in absorbance from Reaction Point 17 to Reaction Point 33.

Example 2

(1) Reaction Specificity of Cholesterol Esterase to LDL and HDL

Figure 2:
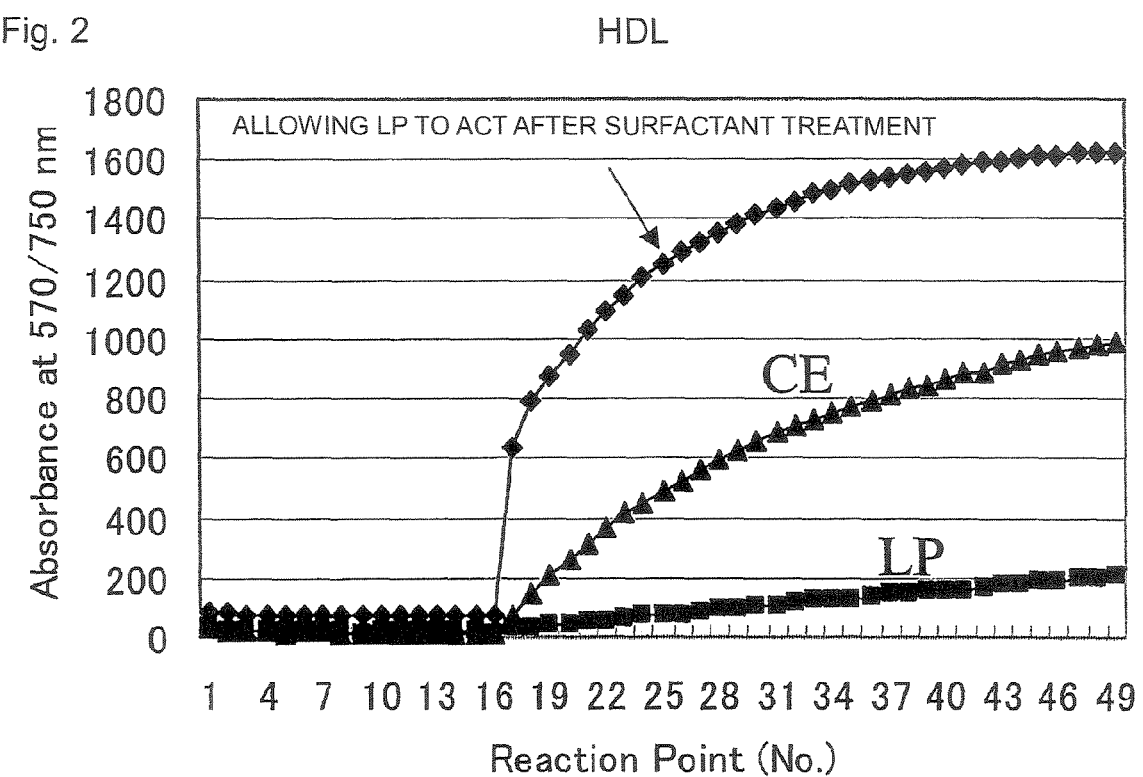
FIG. 2 is a graph showing the reaction specificity with respect to HDL in a case where an LP enzyme is used.

Cholesterol measurement was performed using LDL and HDL which had been treated with 0.1% surfactant (Emulgen, manufactured by Kao Corporation) and the untreated solutions as test samples. The cholesterol esterase used was LP enzyme (with an activity ratio of 512, manufactured by Asahi Kasei Pharma Corporation) or CE enzyme (with an activity ratio of 14.3, manufactured by Amano Enzyme Inc.). LDL and HDL are shown in FIGS. 1 and 2, respectively. The measurement method was according to Example 1. In both cases, when the LP enzyme is used, the reactivity was significantly reduced, relative to the total reactive cholesterol amount (treated with the surfactant). When the CE enzyme was used, high absorption was obtained as compared with the case with the LP enzyme.

Example 3

Figure 3:
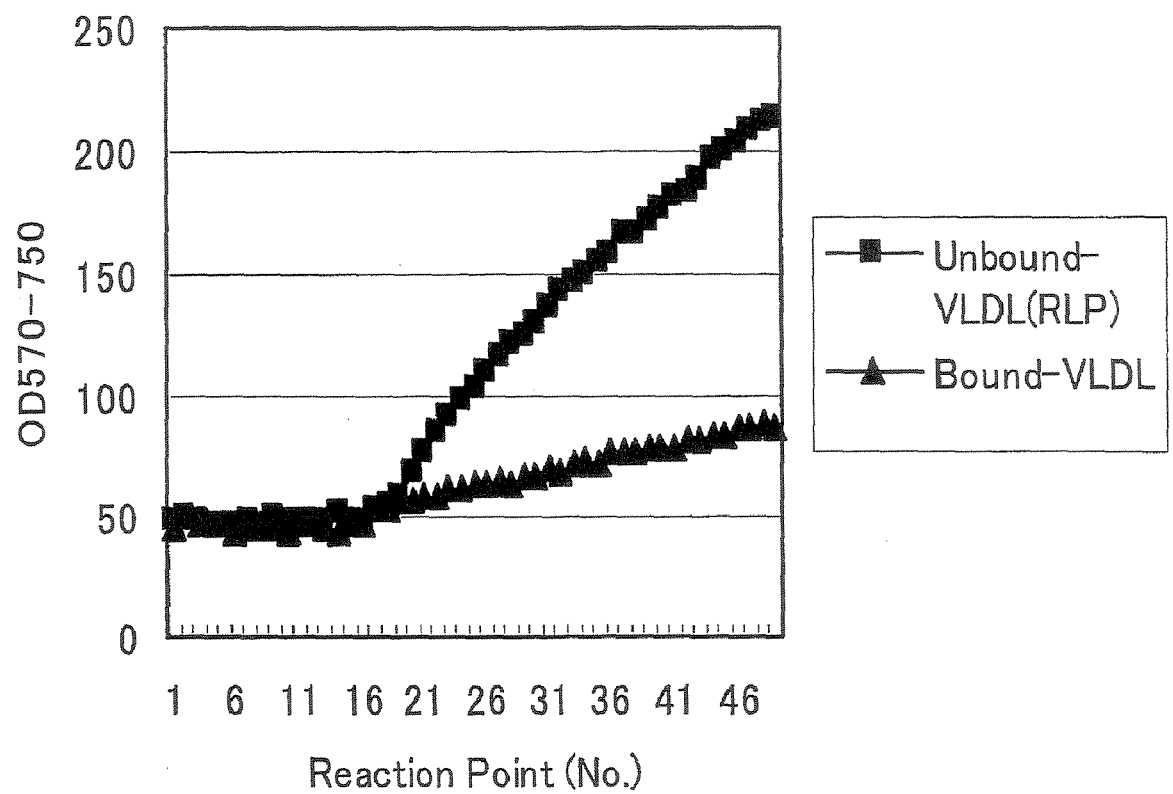
FIG. 3 is a graph showing the reaction specificity with respect to unbound-VLDL and bound-VLDL in the method of the present invention.

(2) Reaction Specificity with Respect to Unbound-VLDL (Remnant-Like Lipoprotein Fraction) and Bound-VLDL In the measurement method according to the present invention, the reaction specificity with respect to the VLDL fraction was examined using the LP enzyme. The measurement method was according to Example 1. FIG. 3 shows the reactivity without addition of the anti-apoB-100 antibody (JI-H) and the anti-apoA-I antibody (H-12) FIG. 4 shows the reactivity with addition of the antibodies. The antibodies were added to the first liquid in such a manner that JI-H and H-12 both reached a final concentration of 100 μg/mL. FIGS. 3 and 4 show substantially the same reaction curve in both Unbound-VLDL and Bound-VLDL, and it was demonstrated that cholesterol in remnant-like lipoprotein was selectively measured. When the antibodies were added, the reactivity of Bound-VLDL was further reduced to about ⅓ so that the enzyme reaction was suppressed.

Thus, it was found that the addition of the antibodies allowed more precise measurement of remnant-like lipoprotein.

Example 4

Comparison with Commercially Available Kit for Measuring Cholesterol in Remnant-Like Lipoprotein (1) Cholesterol in remnant-like lipoprotein in the VLDL fraction was measured using a conventional remnant-like protein measurement kit (RLP-C II, manufactured by JIMRO Co., Ltd.) and different cholesterol esterases (LP with an activity ratio of 512 manufactured by Asahi Kasei Pharma Corporation, LPBP with an activity ratio of 6296 manufactured by Asahi Kasei Pharma Corporation, CEBPM with an activity ratio of 11.2 manufactured by Toyobo Co., Ltd., CEN with an activity ratio of 14.3 manufactured by Asahi Kasei Pharma Corporation, COE 311 with an activity ratio of 31.8 manufactured by Toyobo Co., Ltd.) under the same conditions as in Example 3, and the correlation was determined. The result is shown in Table 1.

As a result, a correlation with the value measured with the already commercially available kit was observed when the four enzymes other than CEBPM were used.

TABLE 3

| CE Name | CE Activity (U/mg) | LPL Activity (U/mg) | LPL/CE Ratio | Automated Correlation (r) |
|---|---|---|---|---|
| LP | 5.8 | 2,970 | 512 | 0.899 |
| LPBP | 0.27 | 1,700 | 6,296 | 0.448 |
| CEN | 153 | 2,190 | 14.3 | 0.520 |
| COE311 | 200 | 6,350 | 31.8 | 0.911 |
| CEBPM | 13.5 | 152 | 11.2 | 0.252 |

Lipoprotein Lipase (LPL) Activity: measured by LP activity analysis (olive oil emulsion).
Cholesterol Esterase (CE) Activity: measured by CE activity analysis (calf blood serum).

(2) Cholesterol in remnant-like lipoprotein in clinical specimens was measured using a conventional remnant-like protein measurement kit (RLP-C II, manufactured by JIMRO Co., Ltd.) and the measurement method of the present invention (using LP (with an activity ratio of 512, manufactured by Asahi Kasei Pharma Corporation) as the cholesterol esterase), and their correlation was determined.

In total 99 specimens (including 14 specimens from healthy subjects, 20 specimens from hyperlipidemia patients including two type III hyperlipidemia patients, and 65 specimens from coronary artery disease patients) were measured by the RLP-C II method and by the Direct RLP-C method at the same time, and the correlations were compared and examined. As a result, a good correlation with the regression line y=0.987x+0.326 and the correlation coefficient r=0.962 was obtained (see FIG. 5).

The invention claimed is:

1. A method for measuring cholesterol in remnant-like lipoprotein, comprising measuring cholesterol in the lipoprotein by measuring hydrogen peroxide or a reduced coenzyme obtained by allowing a cholesterol esterase and a cholesterol oxidase or a cholesterol dehydrogenase to act on a test sample containing a lipoprotein, wherein said cholesterol esterase has lipoprotein lipase activity and cholesterol esterase activity wherein the activity ratio of lipoprotein lipase activity to cholesterol esterase activity ranges from 12:1 to 7000:1.

2. The method according to claim 1, wherein the activity ratio of lipoprotein lipase activity to cholesterol esterase activity ranges from 28:1 to 800:1.

3. The method according to claim 1, wherein the cholesterol esterase is selected from a lipase from *Chromobacterium viscosum* wherein said activity ratio ranges 460:1 to 800:1 identified as LP, a lipase from an unknown microorganism wherein said activity ratio ranges from 5600:1 to 6900:1 identified as LPBP, a cholesterol esterase from *Pseudomonas* sp. wherein said activity ratio ranges from 13:1 to 16:1 identified as CEN, a cholesterol esterase from *Pseudomonas* sp. wherein said activity ratio ranges from 13:1 to 16:1 identified as CE, and a cholesterol esterase from *Pseudomonas* sp. wherein said activity ratio ranges from 28:1 to 35:1 identified as COE 311.

4. The method according to any one of claims 1 to 3, further comprising pretreating the test sample with an anti-apoB-100 antibody and/or an anti-apoA-I antibody.

5. A measuring reagent for cholesterol in remnant-like lipoprotein, comprising:
a cholesterol esterase having lipoprotein lipase activity and cholesterol esterase activity wherein the activity ratio of lipoprotein lipase activity to cholesterol esterase activity ranges from 12:1 to 7000:1; and
a cholesterol oxidase or a cholesterol dehydrogenase.

6. The measuring reagent according to claim 5, wherein the activity ratio of lipoprotein lipase activity to cholesterol esterase activity ranges from 28:1 to 800:1.

7. The reagent according to claim 5, wherein the cholesterol esterase is selected from a lipase from *Chromobacterium viscosum* wherein said activity ratio ranges 460:1 to 800:1 identified as LP, a lipase from an unknown microorganism wherein said activity ratio ranges from 5600:1 to 6900:1 identified as LPBP, a cholesterol esterase from *Pseudomonas* sp. wherein said activity ratio ranges from 13:1 to 16:1 identified as CEN, a cholesterol esterase from *Pseudomonas* sp. wherein said activity ratio ranges from 13:1 to 16:1 identified as CE, and a cholesterol esterase from *Pseudomonas* sp. wherein said activity ratio ranges from 28:1 to 35:1 identified as COE 311.

8. A measuring reagent for cholesterol in remnant-like lipoprotein, comprising;
a first reagent comprising an anti-apoB-100 antibody and/or an anti-apoA-I antibody; and
a second reagent comprising the measuring reagent according to any one of claims 5 to 7.

* * * * *

UNITED STATES PATENT AND TRADEMARK OFFICE
CERTIFICATE OF CORRECTION

| | | |
|---|---|---|
| PATENT NO. | : 7,799,537 B2 | |
| APPLICATION NO. | : 11/720338 | |
| DATED | : September 21, 2010 | |
| INVENTOR(S) | : Takamitsu Nakano et al. | |

It is certified that error appears in the above-identified patent and that said Letters Patent is hereby corrected as shown below:

On the title page, Item (75), the second inventor's last name is incorrect. Item (75) should read:

-- (75) Inventors: Takamitsu Nakano, Maebashi (JP)
                       Manabu Niimi, Takasaki (JP)
                       Fumiko Ogihara, Fujioka (JP) --

Signed and Sealed this
Twenty-eighth Day of December, 2010

David J. Kappos
*Director of the United States Patent and Trademark Office*